United States Patent [19]

Goetz

[11] Patent Number: 4,560,275

[45] Date of Patent: Dec. 24, 1985

[54] PORTABLE INSTANT DISPLAY AND ANALYSIS REFLECTANCE SPECTROMETER

[75] Inventor: Alexander F. H. Goetz, Altadena, Calif.

[73] Assignee: California Institute of Technology, Pasadena, Calif.

[21] Appl. No.: 428,311

[22] Filed: Sep. 29, 1982

[51] Int. Cl.⁴ .............................................. G01J 3/28
[52] U.S. Cl. ................................... 356/326; 250/339; 356/328
[58] Field of Search ............... 356/303, 319, 326, 328; 250/339

[56] References Cited

U.S. PATENT DOCUMENTS

| | | | |
|---|---|---|---|
| 3,100,264 | 8/1963 | Jaffee et al. | 356/326 X |
| 3,829,218 | 8/1974 | Alyanak | 356/326 X |
| 4,273,442 | 6/1981 | Lübbers | 356/303 X |
| 4,365,303 | 12/1982 | Hannah et al. | 356/319 X |

Primary Examiner—F. L. Evans
Attorney, Agent, or Firm—Freilich, Hornbaker, Rosen & Fernandez

[57] ABSTRACT

A portable analysis spectrometer (10) for field mineral identification is coupled to a microprocessor (11) and memory (12) through a bus (13) and A/D converter (14) to display (16) a spectrum of reflected radiation in a band selected by an adjustable band spectrometer (20) and filter (23). A detector array (21) provides output signals at spaced frequencies within the selected spectrometer band which are simultaneously converted to digital form for display. The spectrum displayed is compared with a collection of spectra for known minerals. That collection is stored in memory and selectively displayed with the measured spectrum, or stored in a separate portfolio. In either case, visual comparison is made. Alternatively, the microprocessor may use an algorithm to make the comparisons in search for the best match of the measured spectrum with one of the stored spectra to identify the mineral in the target area.

12 Claims, 5 Drawing Figures

PORTABLE INSTANT DISPLAY AND ANALYSIS REFLECTANCE SPECTROMETER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to reflectance spectrometers, and more particularly to a method and apparatus for instant display and analysis of reflectance spectra for field mineral identification.

Reflectance spectra has been successfully used for identification of many minerals ranging from alunite to zeolite. For example, a portable reflectance spectrometer is disclosed by Dr. Alexander F. H. Goetz, the present inventor, and others, in U.S. Pat. No. 4,043,668. Briefly, the spectrometer disclosed there included an optical unit and a digital recording unit for recording the intensity of reflected radiation at different wavelengths selected by a filter wheel spectral range (0.4 to 2.5 micrometers). The recorded spectral data are later analyzed to determine the composition of the materials which produce the reflectance spectra.

This development of a portable reflectance spectrometer followed the development in 1967-1970 of a Multispectral Photography Experiment S-158 included in the APOLLO 12 mission. That experiment utilized multispectral imaging systems with analysis capability for determination of lunar lithographic boundaries remotely from orbit, but without real-time spectral data analysis. For a description of the experiment see Alexander F. H. Goetz, et al., "Apollo 12 Multispectral Photography Experiment," *Geochimica Acta,* Vol. 3, 2301-2310, MIT Press, 1971.

Following that development, new research programs were established in 1970-1973 to improve the accuracy of telescopic spectroradiometric imaging systems. The role of computer image processing in orbital multispectral photography was established as a means of enhancement. The first preliminary geologic investigations were undertaken in the field on the Colorado plateau to evaluate and interpret earth satellite (ERTS) multispectral data, suitably enhanced. Studies were also carried out to determine the quality and use of ERTS radiometric information with reference to arid desert regions. See Alexander F. H. Goetz, et al., "Symposium ... " Mar. 5-9, 1973 NASA SP-327 at pages 403 to 411, and 1159 to 1167. Also Proceedings of the 4th Annual Conference on Remote Sensing in Arid Lands, 136-147, Univ. of Arizona, Tucson, November. 1973.

After an earth applications effort was formally organized at the Jet Propulsion Laboratory (JPL) of the California Institute of Technology, a novel portable reflectance spectrometer was developed for the 0.4 to 2.5 micrometer range, also based on digital recording of reflectance radiation spectra in the field. This instrument is the subject of the aforesaid U.S. Pat. No. 4,043,668, assigned to California Institute of Technology. The electronic recording unit was a separate "backpack" system, with an inherent time delay prior to actual mineral identification. The unit did not incorporate features of the present invention, and had no instant display capability for analysis, but was capable of recording for later analysis about 200 spectra per day on compact digital tape cassettes. Data thus obtained was further processed at a large trailer or other installation using a programmed digital computer. The disadvantage of that system was that mineral identification could not be made on site, thus creating a problem in correlating the results of data analysis with specific locations of the terrain.

Increased activity from 1975-1978 in the field of multispectral imaging and analysis at JPL led to the development of systems with CCD imaging devices, readily interfaced with more rapid computer analysis and readout systems, as is more fully discussed in U.S. Pat. No. 4,134,683, by Alexander F. H. Goetz, et al. An airborne imaging system including several arrays of charge coupled devices (CCD), or linear detector arrays, were used to obtain simultaneously spectral reflectance data at different wavelengths for a target area using a plurality of filters each accommodating a particular bandwidth. Data from the arrays were read into a computer or microprocessor which made it possible to analyze image data in real time, and to display the information superimposed an an image of terrain data to provide an overlay of mineral identification data on geographic data. However, generally speaking, fairly broad visible and near-IR bands were covered, and only rough qualitative analysis of minerals or oil spill zones was possible. The system was not portable and could be programmed to identify the presence of only one specific material at a time.

The instrument of U.S. Pat. No. 4,134,683 included "band ratioing" using divider circuits. "Band ratioing" is a technique which seeks to provide positive identification of materials by measurement or calculation of ratios of the two most prominent spectral peaks, rather than a single peak, characterizing the material. Band ratioing thus creates ratios of two filtered channels to cancel out topographic effects, etc. Band ratioing is also helpful in dealing with the problem of high data correlation between channels caused by systematic effects such as topography.

Later development described in U.S. Pat. No. 4,345,840, involved in ratioing radiometer able to identify selected materials that reflect radiation within a predetermined band. That instrument is particularly suited for differentiating between the clay minerals most commonly found in the earth's terrain. The instrument is a self-contained dual-beam ratioing radiometer with two optical trains directed at the same target. It provides a continuous digital readout of ratio values from the two optical trains each of which includes a separate filter for selection of the narrow spectral bands to be ratioed for identification of the presence of a particular mineral on the basis of known spectral characteristics of the mineral.

In an exemplary embodiment, the narrow bands ratioed are selected infrared and visible bands in the 0.4 to 2.5 micrometer range, and means are provided for pivoting the axis of at least one optical train with respect to the other, in order that both have their axis directed at the target. Each optical train channel has two relay (repeater) lenses with a selectable filter between the lenses, and a detector at the rear.

As a particular feature of the instrument, two coaxial filter wheels serve the separate channels by providing slits in one filter wheel between filters to pass light to the selected filter in the other wheel, and slits in the other filter wheel between filters to pass light already directed through a selected filter on to a relay lens and detector. In that way, one filter wheel can be rotated independently of the other for particular materials to position a selected filter in the light path between relay lenses while a slit in the other filter wheel passes the filtered light through to the second relay filter and detector. Alternatively, both filter wheels may be turned together, as when the paired filters for particular minerals have been selected and properly disposed on the filter wheels. Operation to check for the presence of the different minerals in the target area can then be simplified by stepping both filter wheels together through all positions, for example five, such that for each position each filter wheel presents a different filter paired with a filter in the other wheel.

Continuous ratioing of the two detector output (division of the detector output of one channel by the detector output of the other channel), and continuous digital readout of the ratio for display and/or recording, permits continuous and instantaneous identification of the material in the field using data tables for specific minerals. For example, kaolinite and montmorillonite yield very different ratio values for filters centered at 2.10 and 2.17 micrometers, and hence the presence of either material can be immediately determined in the field. However, in many clay mineral formations, a large number of individual components are present, including silicates, carbonates, and mixed oxides. In order to perform analysis with that band ratioing device, it becomes necessary to have dozens of filters available in the field, and extensive band ratioing data on selected infrared and visible bands for the known minerals. Hence for field prospecting and identification of minerals an analysis system incorporating some or all of the above-described analysis features, but with greater memory capacity has been desired. In addition, a system for more rapid identification of minerals in formations with complex component mixtures has been desired.

SUMMARY OF THE INVENTION

A portable analysis spectrometer which may be directly calibrated in the field, and then aimed at the mineral formation (illuminated by sunlight or other source of selected band) to provide a display of selected parts of the reflectance spectra is comprised of a means for data processing, a memory and means for display of the reflectance spectra for visible matching with prestored reflectance spectra of known minerals. The same spectrometer without a display means may be employed to identify minerals by using a spectrum matching algorithm to determine the best match of a reflectance spectrum to one of the prestored reflectance spectra in the memory. This spectrometer operating in either mode (visual or algorithm), is made possible by optics directing reflected light at a wavelength adjustable diffraction grating or prism through a selected spectral filter for producing a spectrum over a wavelength section which is then directed by suitable means onto an array of detectors measuring reflectance in narrow contiguous intervals in order to provide a continuous spectrum measurement over the selected section. The output of each detector associated with a different wavelength interval of the selected section is converted to digital form and stored in a memory under control of a microprocessor. The microprocessor may then retrieve the spectrum for display in the visual matching mode or processing in the computer matching mode. In either case, the microprocessor systematically retrieves from memory prestored spectra of known minerals for matching. In the visual mode, each of the prestored spectra is displayed with the input spectrum for visual comparison. In the algorithm mode, each of the prestored spectra is compared by a spectrum matching algorithm which then displays the identity of the mineral that produced the spectrum which best matches the input spectrum. In both cases, it is possible to select only a portion of the spectrum for display. The selected portion may then be expanded in the scales of reflectance and wavelength coordinates, as desired, to make comparison of significant peaks.

The novel features that are considered characteristic of this invention are set forth with particularity in the appended claims. The invention will best be understood from the following description when read in connection with the accompanying drawings.

DESCRIPTION OF PREFERRED EMBODIMENTS

Figure 1:
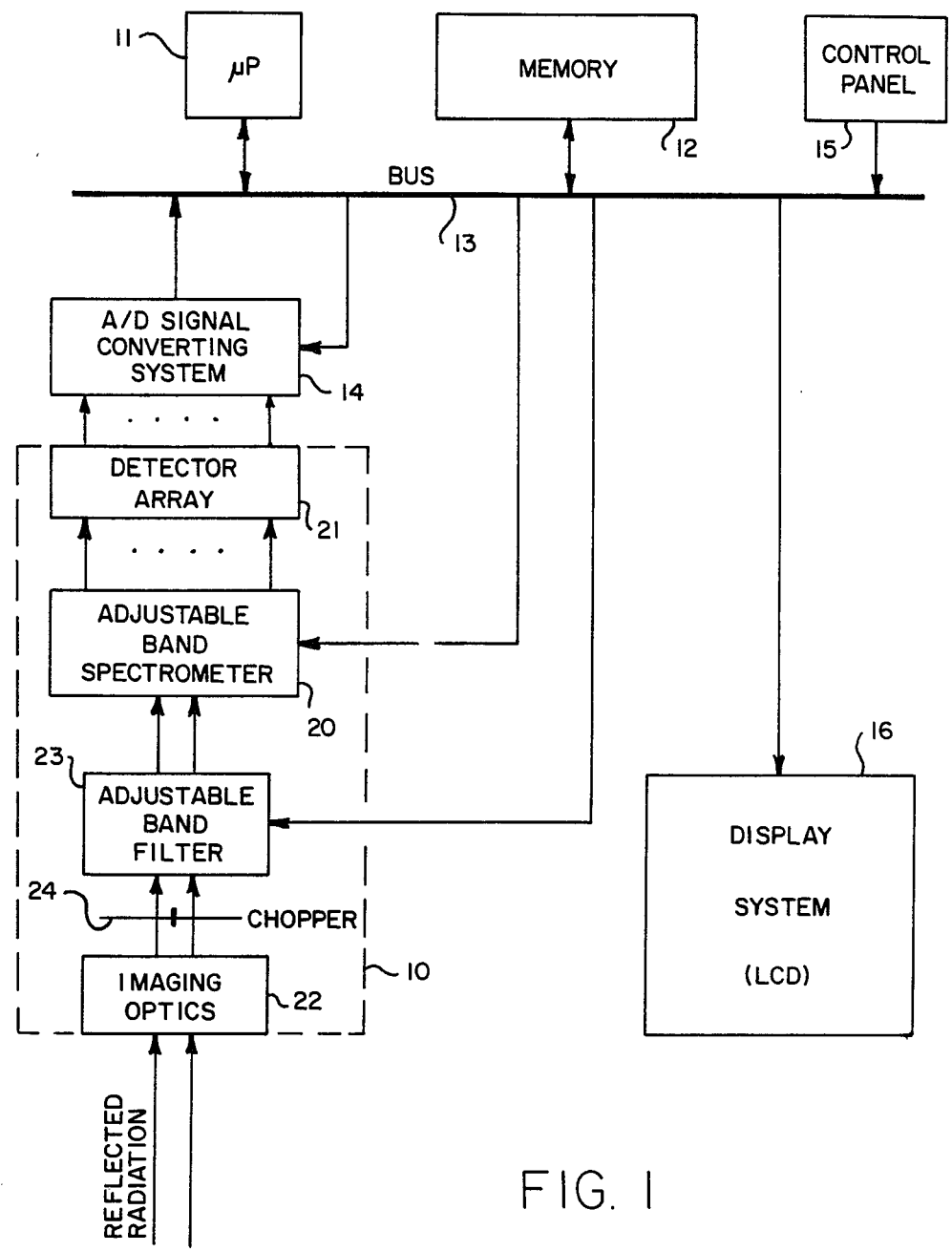
FIG. 1 is a block diagram of a preferred embodiment of the invention.

Referring now to FIG. 1, a portable analysis spectrometer is shown comprising an optical head 10 connected to a microprocessor 11 and memory 12 through a bus 13 by an A/D signal converting system 14. Also connected to the microprocessor and memory is a control panel 15 and display system 16, preferably a liquid crystal display (LCD) system.

The head 10 includes a spectrometer 20 and a detector array 21, such as a linear array of silicon diode detectors. Reflected radiation from the terrain is received by imaging optics 22 focused on the inlet of the spectrometer 20 which is preferably band (wavelength) adjustable, although for the visible near-IR region, a fixed spectrometer could be employed with an array of about 2000 detectors evenly distributed across the complete spectrum. However, for the 1 to 2.5 micron region (short wave IR), a linear array of about 50 detectors is adequate if the spectrometer is adjustable to cover the spectrum in smaller sections, and an adjustable band filter 23 is included between the imaging optics 22 and the spectrometer 20. Optionally included is a chopper 24 which may not be necessary for the visible light region.

The control panel may be used to set the adjustable band filter and spectrometer by entering appropriate commands in the microprocessor which in turn controls the spectrometer 20 and filter 23 through a separate controller included with each. Alternatively, the spectrometer and filter are manually adjusted, and the selected setting is then entered into the microprocessor through the control panel.

Figure 2:
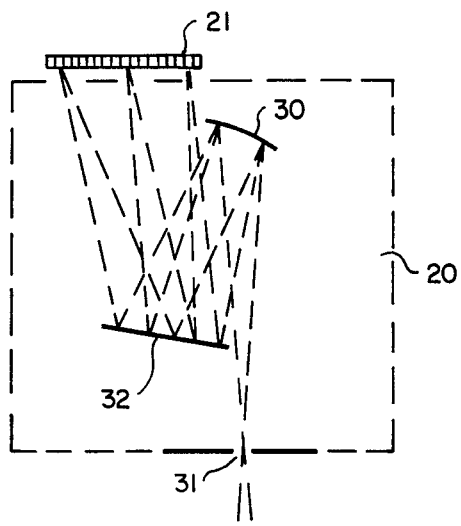
FIG. 2 illustrates schematically an adjustable band spectrometer.

The spectrometer, implemented with a reflection grating or a prism, disperses the light passing through the selected spectral band filter, as shown in FIG. 2 for the case of a concave reflection grating 30. Light passing through a slit 31 is diffracted by the concave reflection grating focused on the array of detectors 21 via a folding mirror 32. This use of a concave reflection grating first developed by Rowland obviated the need for a collimating lens between the slit and the grating, and the need for a telescope between the grating and the detector array because of the focusing effect of the concave grating. By tilting the grating 30 relative to the mirror 32, the diffracted light can be adjusted relative to the detector array 20 so that for the 1 to 2.5 micron region, an array of about 50 detectors will be adequate to cover the spectrum in sections, as mentioned above. Many other known arrangements are possible for the spectrometer, both with a reflection grating and with a prism.

The signal from each detector is converted from analog to digital form by separate converters in the A/D signal converting system 14. Separate converters are preferred for each detector so that the intensity of light received by each will be proportionate to the intensity of light being reflected by the terrain. The operator initiates the process by a push-button command to the microprocessor, which in turn initiates the A/D conversion process for each detection. By using the successive approximation technique, the process is completed for each detector in the same number of clock pulses used throughout the digital portions of the system. The microprocessor then begins the process of reading in the digital value of the intensity of each detector. These values, which constitute a spectrum, are stored by the microprocessor in the memory 12 for display and analysis.

Figure 3A:
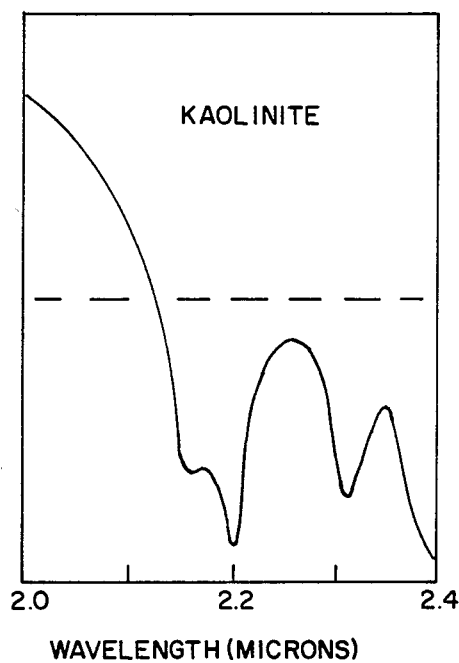
FIGS. 3a, b and c are illustrative graphs of radiation reflectance spectra of selected minerals which are stored for comparison with a displayed spectrum to determine the mineral of a reflecting target area in the field using the instrument of FIG. 1.
Figure 3B:
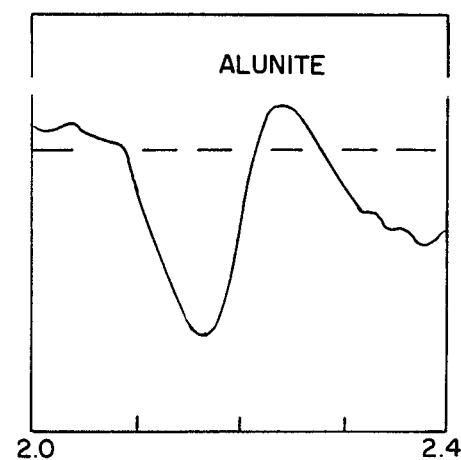
Figure 3C:
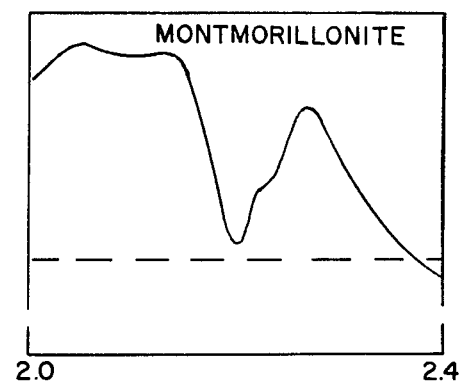

Identification of unknown materials in the field can be carried out by locating significant peaks in the spectrum on the display 16, and visually matching an observed spectrum to spectra stored in the memory 12 or a hard-copy reference portfolio. FIGS. 3a, b and c illustrate typical spectra stored in a hard-copy reference library for kaolinite, montmorillonite, and alunite in the 2.0 to 2.5 micrometer region. A spectrum of reflected radiation displayed may be compared by the operator with these stored spectra. A match with one of these stored spectra will thus indicate the mineral in the target area that produced the reflectance spectra stored using spectral filters for that region. Alternately the user can selectively call up from memory prerecorded spectra, and by blink comparison on the display 16, visually determine the best match. Once a sizable library of reference spectra is accumulated, a spectrum matching algorithm programmed into the microprocessor 18 can rapidly identify materials.

Allowance can be made for a wide variation of spectral response conditions, and for sequential identification of the individual components in mixed materials. The system will quickly detect the presence of all types of mineral and other materials for which spectral responses are known, such as plants. Initial calibration is carried out in ambient light, preferably with a target illuminated by the sun. If an adjustable grating is present, the grating is adjusted to a desired initial wavelength band, and the corresponding band filter is selected. For a fixed grating spectrometer the appropriate broadband filter is installed. Then the instrument is pointed at the standard reflectance calibration target, such as a white ceramic wool sold commercially under the trademark FIBERFAX which uniformly reflects all wavelengths. The microprocessor is programmed to automatically adjust the gains for each detector to equal a selected 100% level.

The instrument is then pointed at the target for display of the spectrum on screen 11. Also displayed on the ordinate are wavelength values for the selected band. Prerecorded spectra are then called up for display either in a blink mode or as a superimposed curve for comparison with the measured spectrum. The operator causes the microprocessor to step from one prerecorded spectrum to the next in search for the best mode. Also displayed with each prerecorded spectrum is the identification of the material which yielded that spectrum. Alternatively, the microprocessor may be commanded by the operator through the control panel to use its stored algorithm to obtain the best match with a prerecorded spectrum, and thus identify the material reflecting light in the selected band.

In those cases where the entire measured spectrum is displayed, such as when using a fixed spectrometer, the operator will first select a band of the displayed spectrum encompassing significant peaks for amplification and display. Identification of the material reflecting light in that band is then identified. In this manner components of material are identified individually.

Although particular embodiments of the invention have been described and illustrated herein, it is recognized that modifications and variations may readily occur to those skilled in the art. Consequently, it is intended that the claims be interpreted to cover such modifications and equivalents.

What is claimed is:

1. A method for providing field identification of particular reflecting materials in mineral formations by identification of a high resolution reflectance spectrum in a selected wavelength section using a spectrometer and an array of detectors for measuring reflectance in narrow contiguous intervals in order to provide a continuous spectrum measurement over the selected section, each selected section being chosen for a particular spectral characteristic of a material of interest, comprising the steps of storing characteristics spectra over selected wavelength sections for each of a group of particular reflecting materials, selecting a wavelength section of reflectance to be analyzed in the field by measurement of light at different wavelengths within said section using said spectrometer and array of detectors thereby to obtain a reflectance spectrum, and comparing said reflectance spectrum with individual ones of said stored characteristic spectra to determine which best matches said reflectance spectrum, thus identifying a particular material in said mineral formation giving rise to the reflectance spectrum in a selected section.

2. A method as defined in claim 1 wherein the intensity of reflected light at each of different wavelengths within said selected section measured by said array of detectors is determined simultaneously from said reflectance spectrum.

3. A method as defined in claim 2 using a programmed data processing system comprising a microprocessor, a memory and means for displaying data stored in said memory under control of said microprocessor, said data processor including a control panel to allow an operator to direct operation of said data processing system, wherein said reflectance spectrum is stored in said memory for display by said means for display under control of said operator via said control panel.

4. A method as defined in claim 3 wherein said stored spectra are stored in said memory and displayed individually with said stored reflectance spectrum for visual comparison.

5. A method as defined in claim 2 using a programmed data processing system comprising a microprocessor, a memory and control panel to allow an operator to direct operation of said data processing system, wherein said reflectance spectrum and said stored spectra are stored in said memory for comparison of said reflectance spectrum with each of said stored spectra for identification of best match under control of said operator through said control panel, thereby to identify a particular material in said mineral formation.

6. Apparatus for providing field identification of particular reflecting materials in minerals formations by identification of reflectance spectrum in a selected wavelength section using a spectrometer meter and an array of detectors, each section being chosen for a particular spectral characteristic of a material of interest selected from a group for which reflectance spectra are stored for comparison, comprising means for selecting from predetermined wavelength sections a series of contiguous narrow wavelength intervals of reflectance to be analyzed by measurement of light at said series of contiguous narrow wavelength intervals within said section using said spectrometer and array of detectors, means for simultaneously measuring reflectance detected by each detector of said array thereby to obtain a high resolution reflectance spectrum, and means for comparing said reflectance spectrum with individual ones of said stored spectra to determine which best matches said reflectance spectrum, thus identifying a particular material in said mineral formation giving rise to the reflectance measured at a selected section reflectance.

7. Apparatus as defined in claim 6 including means for storing said reflectance spectrum, and means for displaying said stored reflectance spectrum.

8. Apparatus as defined in claim 7 wherein said stored reflectance spectra are stored in a portfolio for visual comparison with a displayed spectrum.

9. Apparatus as defined in claim 7 including a programmed data processing system comprising a microprocessor, and said means for storing said reflectance spectrum also stores said stored reflectance spectrum, wherein said stored spectra are taken from said memory for display individually with said stored reflectance spectrum for visual comparison.

10. Apparatus as defined in claim 9 further including a control panel to allow an operator to direct operation of said data processing system, whereby said reflectance spectrum and said stored spectra are read from said memory for visual comparison of said reflectance spectrum with each of said stored spectra individually for identification of best match under control of said operator through said control panel, thereby to identify a particular material in said mineral formation.

11. Apparatus as defined in claim 6, 7, 8 or 9 wherein said spectrometer is adjustable for said wavelength band selected.

12. Apparatus as defined in claim 11, including an adjustable filter in front of said spectrometer, said filter being adjusted for a section which includes said said predetermined wavelength sections.

* * * * *